(12) United States Patent
Davidsen et al.

(10) Patent No.: US 9,237,880 B2
(45) Date of Patent: Jan. 19, 2016

(54) COMPOSITE ACOUSTIC BACKING WITH HIGH THERMAL CONDUCTIVITY FOR ULTRASOUND TRANSDUCER ARRAY

(75) Inventors: Richard Edward Davidsen, Andover, MA (US); Wojtek Sudol, Andover, MA (US)

(73) Assignee: Koninklijke Philips N.V., Eindhoven (NL)

( * ) Notice: Subject to any disclaimer, the term of this patent is extended or adjusted under 35 U.S.C. 154(b) by 205 days.

(21) Appl. No.: 13/415,377

(22) Filed: Mar. 8, 2012

(65) Prior Publication Data

US 2012/0238880 A1    Sep. 20, 2012

Related U.S. Application Data

(60) Provisional application No. 61/453,690, filed on Mar. 17, 2011.

(51) Int. Cl.
*A61B 8/00* (2006.01)
*B06B 1/06* (2006.01)
*G10K 11/00* (2006.01)

(52) U.S. Cl.
CPC .............. *A61B 8/4494* (2013.01); *A61B 8/4483* (2013.01); *B06B 1/0629* (2013.01); *G10K 11/002* (2013.01)

(58) Field of Classification Search
CPC .. A61B 8/4483; A61B 8/4494; A61B 8/4444; A61B 8/4488; A61B 8/546
USPC .................. 600/437, 459; 310/341; 29/25.35
See application file for complete search history.

(56) References Cited

U.S. PATENT DOCUMENTS

| | | | |
|---|---|---|---|
| 4,297,607 A | 10/1981 | Lynnworth et al. | |
| 5,560,362 A | 10/1996 | Sliwa | |
| 6,551,247 B2 * | 4/2003 | Saito et al. | 600/459 |
| 7,348,713 B2 * | 3/2008 | Hashimoto | 310/334 |
| 7,567,016 B2 * | 7/2009 | Lu et al. | 310/322 |
| 7,755,255 B2 * | 7/2010 | Saito et al. | 310/334 |
| 8,232,705 B2 * | 7/2012 | Tai | 310/334 |
| 8,376,950 B2 * | 2/2013 | Nagano et al. | 600/459 |
| 2003/0029010 A1 * | 2/2003 | Aime | 29/25.35 |
| 2003/0032884 A1 * | 2/2003 | Smith et al. | 600/459 |
| 2004/0100163 A1 * | 5/2004 | Baumgartner et al. | 310/334 |
| 2005/0275313 A1 | 12/2005 | Yamashita et al. | |
| 2006/0084966 A1 * | 4/2006 | Maguire et al. | 606/41 |
| 2006/0186765 A1 | 8/2006 | Hashimoto | |
| 2006/0261707 A1 * | 11/2006 | Wildes et al. | 310/346 |
| 2008/0188755 A1 | 8/2008 | Hart | |

(Continued)

FOREIGN PATENT DOCUMENTS

| | | |
|---|---|---|
| JP | 2000165995 | 6/2000 |
| WO | 2009083896 A2 | 7/2009 |

*Primary Examiner* — Baisakhi Roy

(57) ABSTRACT

A backing block for an ultrasonic transducer array stack of an ultrasound probe is formed as a composite structure of material of high thermal conductivity in which is embedded a structure of acoustic dampening material. In a constructed embodiment the composite structure is formed from a block of thermally conductive graphite in which a plurality of cylindrical holes are formed which are filled with acoustic dampening material. The holes are angled in relation to the Z-axis direction from the rear of the transducer stack so that reverberation energy traveling in that direction will encounter acoustic dampening material. The graphite around the holes is effective to conduct heat to the rear of the probe and away from the transducer stack and its ASIC.

14 Claims, 4 Drawing Sheets

(56) References Cited

U.S. PATENT DOCUMENTS

2009/0062656 A1 3/2009 Hyuga
2010/0168581 A1 7/2010 Knowles et al.
2011/0181149 A1* 7/2011 Shikata ................. 310/327
2011/0198151 A1* 8/2011 Oakley et al. ............. 181/290
2012/0181902 A1* 7/2012 Gelly et al. ................ 310/341

* cited by examiner

COMPOSITE ACOUSTIC BACKING WITH HIGH THERMAL CONDUCTIVITY FOR ULTRASOUND TRANSDUCER ARRAY

This invention relates to medical diagnostic ultrasound systems and, in particular, to backing materials for an ultrasonic transducer array.

Two dimensional array transducers are used in ultrasonic imaging to scan in three dimensions. Two dimensional arrays have numerous rows and columns of transducer elements in both the azimuth and elevation directions, which would require a large number of cable conductors to couple signals between the probe and the mainframe ultrasound system. A preferred technique for minimizing the number of signal conductors in the probe cable is to perform at least some of the beamforming in the probe in a microbeamformer ASIC (application specific integrated circuit.) This technique requires only a relatively few number of partially beamformed signals to be coupled to the mainframe ultrasound system, thereby reducing the required number of signal conductors in the cable. However a large number of signal connections must be made between the two dimensional array and the microbeamformer ASIC. An efficient way to make these connections is to design the transducer array and the ASIC to have flip-chip interconnections, whereby conductive pads of the transducer array are bump bonded directly to corresponding conductive pads of the ASIC.

The high density electronic circuitry of the microbeamformer ASIC can, however, produce a significant amount of heat in its small IC package, which must be dissipated. There are two main directions in which this heat can flow. One direction is forward through the acoustic stack toward the lens at the patient-contacting end of the probe. Thermal conductivity is aided in this direction by electrically conductive elements in the transducer stack. This forward path exhibits relatively low resistance to thermal flow. Build-up of heat in the lens must then be prevented by reducing transmission voltage and/or the pulse repetition frequency, which adversely affects probe performance.

The preferred thermal conduction direction is to the rear, away from the lens and toward a heat spreader (typically aluminum) at the rear of the probe. But generally located behind the transducer stack, the array elements and the microbeamformer ASIC, is an acoustic backing block. The purpose of the acoustic backing block is to attenuate ultrasonic energy emanating from the rear of the acoustic stack and prevent this energy from causing reverberations that are reflected toward the acoustic stack. An acoustic backing block is generally made of a material with good acoustic attenuation properties such as an epoxy loaded with micro-balloons or other sound-deadening particles. Such materials, however, typically have poor thermal conductivity. Hence it is desirable to provide an acoustic backing block for an ultrasound probe which exhibits good acoustic attenuation of acoustic energy entering the block, good thermal conductivity toward the rear of the probe and away from the lens, good mechanical structure which can support the acoustic stack as needed, and appropriate electrical isolation of the microbeamformer ASIC from other conductive components of the probe.

In accordance with the principles of the present invention, a backing block for an ultrasonic transducer array stack is formed of a matrix of a highly thermally conductive material with internal acoustic damping members. A preferred material for the thermally conductive material is graphite exhibiting a high thermal conductivity. The graphite can be formed into a rigid block with the mechanical stability to support a transducer array stack. The internal acoustic damping members, which can be formed by drilling holes in the graphite block which are filled with acoustic damping material, are preferably located such that an acoustic wave traveling normal to the rear surface of the transducer array stack must encounter an acoustic damping member and be acoustically attenuated. An electrically isolating layer can be located on the top or bottom of the backing block as needed.

Figure 1:
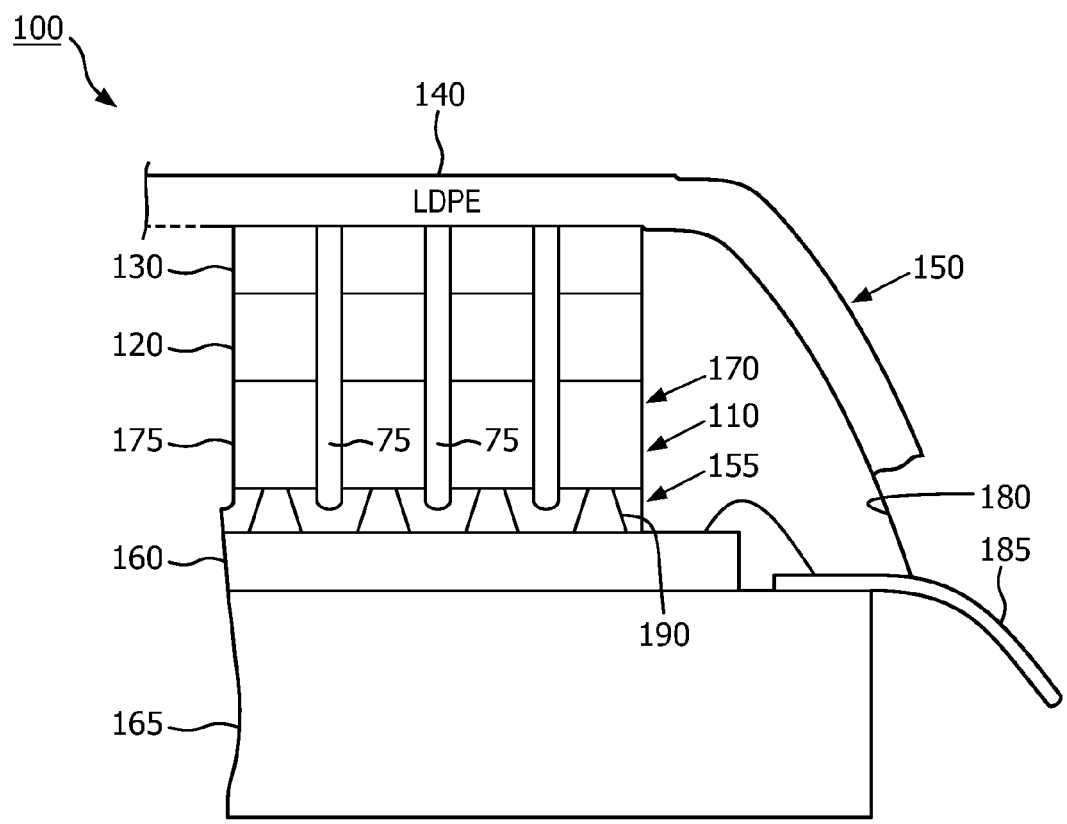
FIG. 1 illustrates an acoustic stack with a thermally conductive backing block constructed in accordance with the principles of the present invention.

Referring first to FIG. 1, an acoustic stack 100 with a thermally conductive backing block which is constructed in accordance with the principles of the present invention is shown schematically. A piezoelectric layer 110 such as PZT and two matching layers bonded to the piezoelectric layer are diced by dicing cuts 75 to form an array 170 of individual transducer elements 175, four of which are seen in FIG. 1. The array 170 may comprise a single row of transducer elements (a 1-D array) or be diced in two orthogonal directions to form a two-dimensional (2D) matrix array of transducer elements. The matching layers match the acoustic impedance of the piezoelectric material to that of the body being diagnosed, generally in steps of progressive matching layers. In this example the first matching layer 120 is formed as an electrically conductive graphite composite and the second matching layer 130 is formed of a polymer loaded with electrically conductive particles. A ground plane 180 is bonded to the top of the second matching layer, and is formed as a conductive layer on a film 150 of low density polyethylene (LDPE) 140. The ground plane is electrically coupled to the transducer elements through the electrically conductive matching layers and is connected to a ground conductor of flex circuit 185. The LDPE film 150 forms the third and final matching layer 140 of the stack.

Below the transducer elements is an integrated circuit 160, an ASIC, which provides transmit signals for the transducer elements 175 and receives and processes signals from the elements. Conductive pads on the upper surface of the integrated circuit 160 are electrically coupled to conductive pads on the bottoms of the transducer elements by stud bumps 190, which may be formed of solder or conductive epoxy. Signals are provided to and from the integrated circuit 160 by connections to the flex circuit 185. Below the integrated circuit 160 is a backing block 165 which attenuates acoustic energy emanating from the bottom of the transducer stack. In accordance with the principles of the present invention, the backing block also conducts heat generated by the integrated circuit away from the integrated circuit and the transducer stack and away from the patient-contacting end of the transducer probe.

Figure 2:
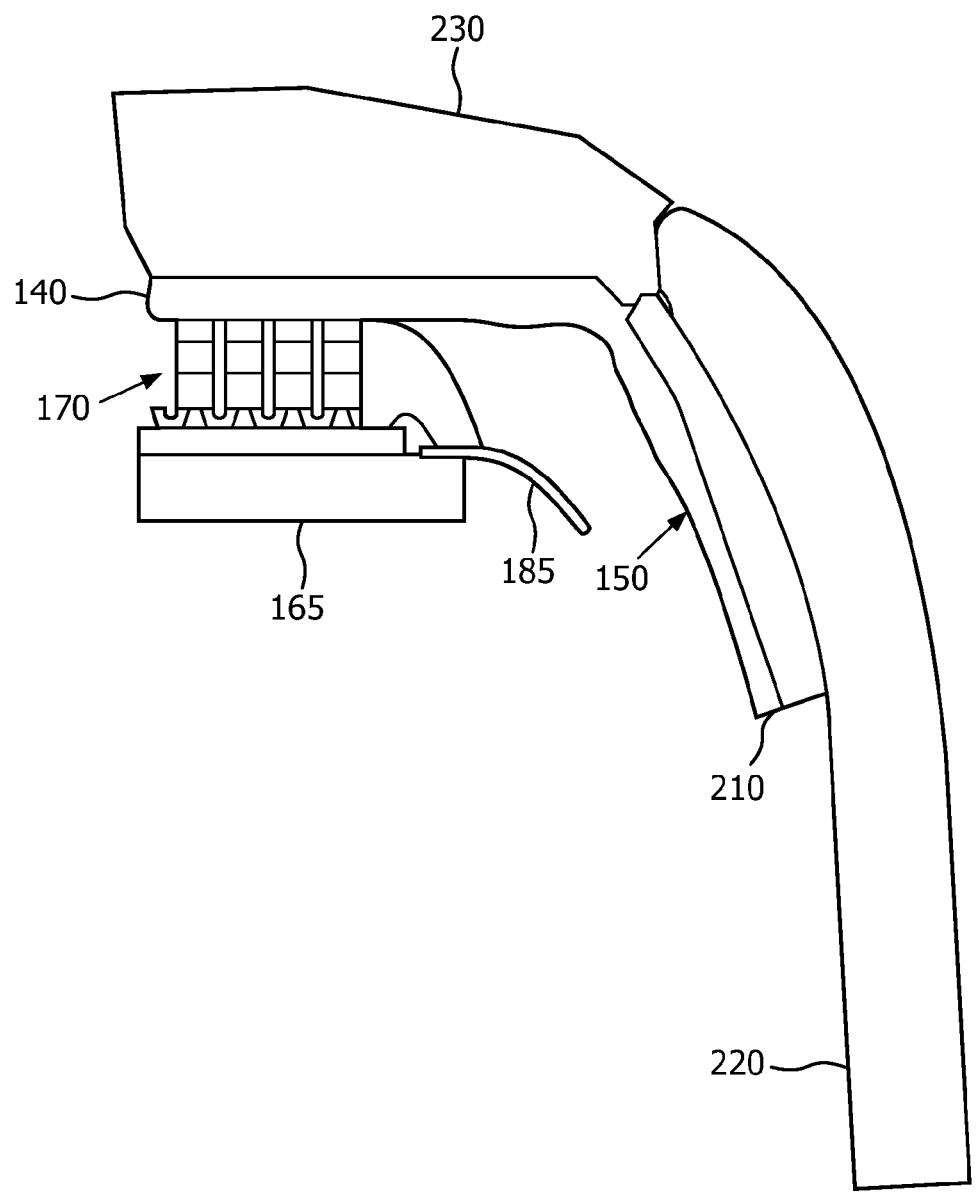
FIG. 2 illustrates the acoustic stack of FIG. 1 when assembled in a transducer probe with a lens cover.

FIG. 2 illustrates the transducer stack assembly of FIG. 1 when assembled inside a transducer probe. In the probe of FIG. 2 the third matching layer 140 is bonded to the acoustic lens 230. Ultrasound waves are transmitted through the lens 230 and into the patient's body during imaging, and echoes received in response to these waves are received by the transducer stack through the lens 230. The LDPE film 150 serves to enclose the transducer stack in this embodiment as it is wrapped around the stack and bonded by an epoxy bond 210 to the probe housing 220. Further details of this construction are found in US patent publication no. US 2010/0168581 (Knowles et al.)

A preferred implementation for the backing block 165 is illustrated in the remaining drawings. A preferred backing block 165 starts with a block of graphite 20. Other alternatives include graphite loaded with metals such as nickel or copper which provide good machinability and favorable thermal properties. The graphite block 20 is used to form a composite backing structure which satisfies a number of performance objectives. First, the backing structure must have good Z-axis thermal conductivity. Graphite has good thermal conductivity, a Tc of 80 to 240 W/m° K at 0° C.-100° C. For conduction parallel to the crystal layers, Tc will approach 1950 W/m° K at 300° K. The Z-axis direction is the direction back and away from the transducer stack 100 and the integrated circuit 160. Thus, it is desirable to align the crystal layers of the graphite block 20 for heat flow in the Z-axis direction. In other implementations it may be desirable to preferentially conduct heat laterally or both laterally and in the Z-axis direction, in which case a different direction of crystal alignment may be desired or the alignment direction may be immaterial to the design. When aluminum is used to dissipate some of the heat, which may be by use of an aluminum heat spreader or an aluminum frame inside the probe housing, it is desirable for the thermal conductivity of the backing block be comparable to or better than that of aluminum, so that heat will preferentially flow to the aluminum. Aluminum has a comparable Tc of 237 W/m° K at room temperature, so this performance objective is well met by a graphite block 20.

A second objective is that the backing block provide structural support for the acoustic stack 100 and integrated circuit 160. A graphite block is structurally sound, satisfying this objective.

A third objective is to provide electrical isolation of the integrated circuit 160 from the aluminum member or frame of the probe. Graphite, being electrically conductive, can satisfy this objective by coating the backing block with a non-conductive insulative coating. In some implementations it may be desirable to coat only the side of the block which is in contact with the transducer stack. In other implementations it may be desirable to coat multiple sides of the backing block. It may be desirable, for instance, to coat the lateral sides of the block with an insulative acoustic damping material which would provide the additional benefit of suppressing lateral acoustic reverberation.

Figure 3:
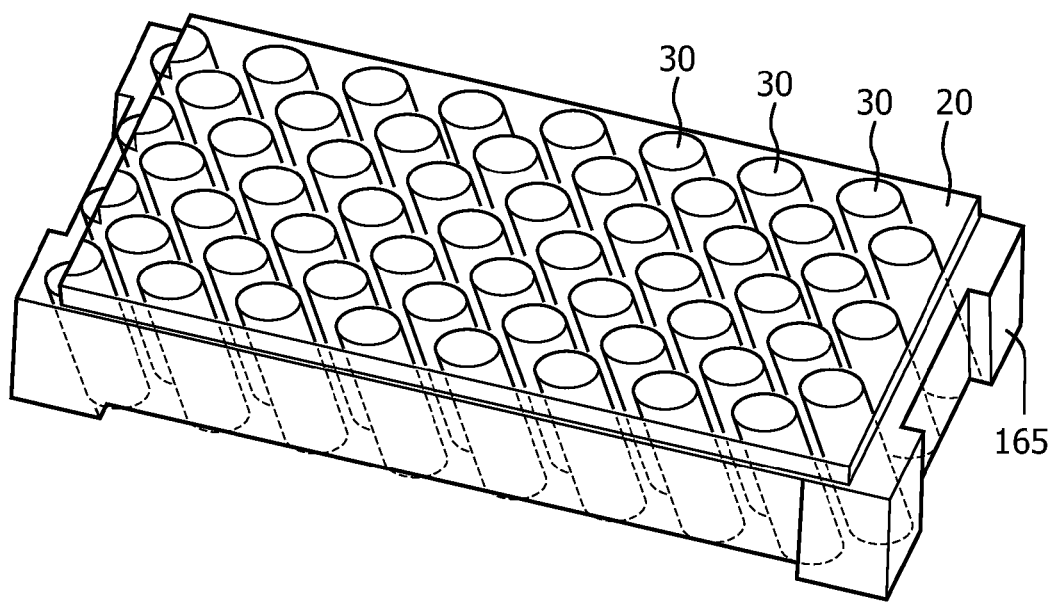
FIG. 3 is a perspective view of a thermally conductive backing block constructed in accordance with the principles of the present invention.
Figure 4:
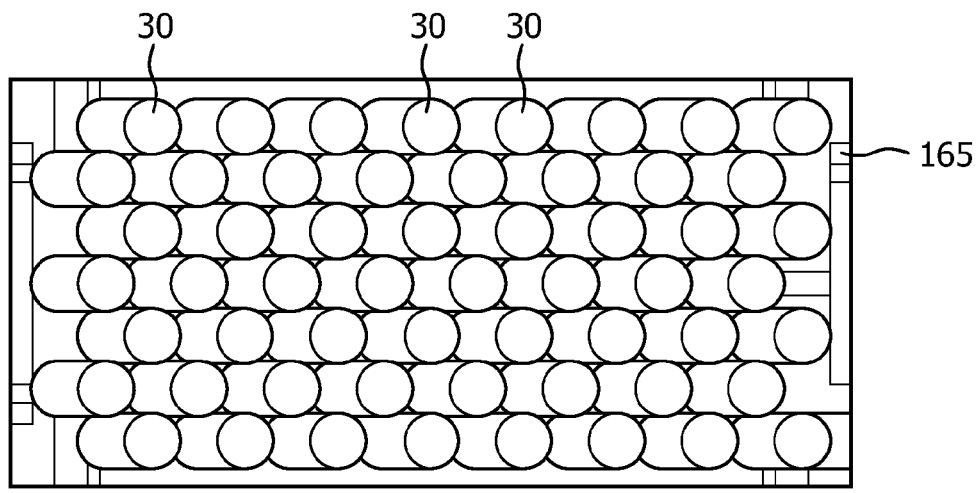
FIG. 4 is a top plan view of a thermally conductive backing block constructed in accordance with the principles of the present invention.
Figure 5:
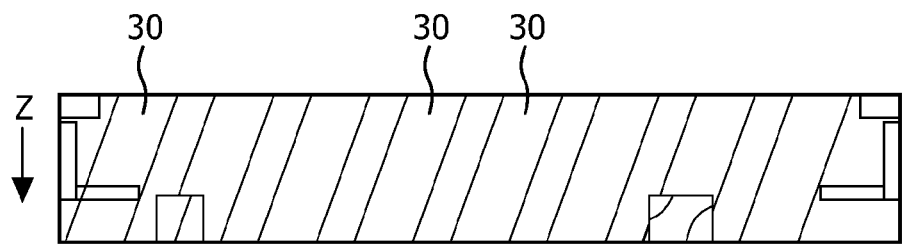
FIG. 5 is a side cross-sectional view of a thermally conductive backing block constructed in accordance with the principles of the present invention.

The fourth objective is that the backing block must dampen acoustic energy entering the block. Graphite is a good conductor of acoustic energy and provides very little inherent acoustic damping. This objective is satisfied by employing the graphite block as the framework for a composite structure of internal acoustic dampening members as shown in FIGS. 3, 4, and 5. In these drawings the graphite is rendered translucent for clarity of illustration of the internal composite structure of the block. The dampening members are formed as a plurality of angled cylinders 30 of backing material in the backing block. The cylinders 30 are cut or drilled into the graphite block 20, then filled with acoustic dampening material such as epoxy filled with micro balloons or other acoustic damping particles. As the top plan view of the backing block of FIG. 4 illustrates, the tops of the cylinders 30 present a large area of acoustic dampening material to the back of the integrated circuit. A considerable amount of the undesired acoustic energy emanating from the back of the integrated circuit and acoustic stack will thus pass immediately into the dampening material. The angling of the cylinders as seen in FIG. 3 and best seen in the cross-section view of FIG. 5 assures that acoustic energy traveling in the Z-axis direction will have to intersect dampening material at some point in the path of travel. Preferably, there is no path in the Z-axis direction formed entirely of graphite, and the angling of the cylinders does not promote reflection of energy back to the integrated circuit but provides scattering angles downward and away from the integrated circuit. In practice it may be sufficient to block most of the Z-axis pathways such as by blocking 95% of the pathways. Thus, the angling of the cylinders assures damping of all or substantially all of the Z-axis directed energy.

Heat, however, will find continuous pathways through the graphite between the cylinders 30. Since the flow of heat is from higher temperature regions to lower (greater thermal density to lesser), heat will flow away from the integrated circuit 160 and acoustic stack 100 to structures below the backing block 165 where it may be safely dissipated.

Other materials may be used for the thermally conductive material of the backing block, such as aluminum, graphite foam, or aluminum nitride. The pattern, size and spacing of the holes filled with dampening material can also be varied and optimized for performance and manufacturability. While drilling will produce circular holes, other hole shapes such as rectangular or triangular may alternatively be used. If it is desired or necessary to electrically isolate an electrically conductive backing block from other components of the probe such as the integrated circuit, a layer of non-conductive materials such as parylene, aluminum nitride, or polyimide can be added to one or more external surfaces of the backing block or constructed internal to the block. A lateral composite structure of dampening materials which is not arranged in cylindrical angled holes can alternatively be used, so long as there are no flat surfaces in parallel with the top and bottom surfaces of the block which would reflect acoustic energy back toward the integrated circuit and acoustic stack.

What is claimed is:
1. An ultrasonic transducer array assembly comprising:
an array of transducer elements configured to transmit ultrasound ultrasonic waves in a forward desired direction and a rearward undesired ultrasonic emission direction;
a composite backing block, located rearward of the array of transducer elements, the composite backing block comprising a backing block material comprising graphite having crystals that are aligned so as to conduct heat away from the array of transducer elements in a Z-axis direction that is normal to a rear surface of the array and spanning a depth of the composite backing block; and
a composite structure comprising acoustic dampening members located in the composite backing block,
wherein the acoustic damping members are located in the composite backing block such that all or substantially all ultrasonic emissions in the rearward direction intersect at least a portion of the acoustic dampening members, and wherein the acoustic damping members comprise a plurality of cylinders filled with acoustic dampening material, oriented at a non-parallel angle in relation to the Z-axis direction, and spanning the depth of the composite backing block.
2. The ultrasonic transducer array assembly of claim 1, wherein heat is conducted by the backing block material to a metallic structure.

3. The ultrasonic transducer array assembly of claim 1, wherein the acoustic dampening material in the cylinders at the top surface comprises a majority of the area of the top surface.

4. The ultrasonic transducer array assembly of claim 1, wherein the cylinders are angled at an angle which causes acoustic energy traveling in the rearward direction to be scattered away from the array of transducer elements.

5. The ultrasonic transducer array assembly of claim 1, wherein a surface of the composite backing block is coated with a layer of non-conductive material.

6. The ultrasonic transducer array assembly of claim 5, wherein the layer of non-conductive material further comprises acoustic damping material.

7. The ultrasonic transducer array assembly of claim 1, further comprising an integrated circuit electrically coupled to the rear of the array of transducer elements, wherein the composite backing block is in thermally conductive contact with the integrated circuit.

8. The ultrasonic transducer array assembly of claim 7, wherein the array of transducer elements further comprises a 2D array of transducer elements; and wherein a surface of the composite backing block is in contact with a surface of the integrated circuit.

9. The ultrasonic transducer array assembly of claim 1, wherein the backing block conducts heat to an aluminum heat spreader, and wherein the composite backing block material exhibits a thermal conductivity comparable to or better than that of aluminum.

10. The ultrasonic transducer array assembly of claim 1, wherein the composite backing block material is graphite, and wherein the graphite backing block material is thermally coupled to a metallic member inside an ultrasound probe.

11. The ultrasonic transducer array assembly of claim 1, wherein the composite backing block further provides structural support for an acoustic stack comprising the array of transducer elements.

12. The ultrasonic transducer array assembly of claim 11, wherein the acoustic stack further comprises an integrated circuit, wherein the composite backing block acts to conduct heat produced by the integrated circuit away from the acoustic stack.

13. The ultrasonic transducer array assembly of claim 1, wherein the composite backing block comprises a top side and a bottom side and at least some of the acoustic dampening members span from the top side to the bottom side of the backing block.

14. The ultrasonic transducer array assembly of claim 1, wherein the acoustic dampening members are oriented in the composite backing block such that ultrasound emissions traveling in the rearward direction are deflected away from the array of transducer elements.

* * * * *